(12) United States Patent
Macfarlane et al.

(10) Patent No.: US 6,593,145 B2
(45) Date of Patent: Jul. 15, 2003

(54) DENSITY GRADIENT SOLUTIONS OF METAL ION CHELATE COMPLEXES

(75) Inventors: Ronald D. Macfarlane, Temple, TX (US); Brian D. Hosken, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/092,032

(22) Filed: Mar. 6, 2002

(65) Prior Publication Data

US 2002/0166815 A1 Nov. 14, 2002

Related U.S. Application Data

(60) Provisional application No. 60/274,045, filed on Mar. 7, 2001.

(51) Int. Cl.$^7$ .......................... G01N 9/30; B01D 21/26; B01D 17/38
(52) U.S. Cl. .................. 436/177; 210/639; 210/787; 252/182.32; 252/182.34; 436/8; 436/17; 436/45; 436/71
(58) Field of Search ....................... 436/45, 71, 177, 436/8, 17; 422/72; 210/639, 787; 252/182.32, 182.34

(56) References Cited

U.S. PATENT DOCUMENTS

| | | | |
|---|---|---|---|
| 4,167,955 A | 9/1979 | Sharples | 141/1 |
| 4,290,300 A | 9/1981 | Carver | 73/32 |
| 4,480,038 A | 10/1984 | Cheng | 435/261 |
| 4,945,040 A | * 7/1990 | Fless et al. | 435/7.94 |
| 5,489,386 A | 2/1996 | Saunders | 210/514 |
| 5,641,622 A | * 6/1997 | Lake et al. | 435/2 |
| 5,728,412 A | * 3/1998 | Fujii et al. | 426/11 |
| 5,840,502 A | 11/1998 | Van Vlasselaer | 435/7.21 |
| 5,985,037 A | 11/1999 | Dorin et al. | 127/29 |
| 6,083,750 A | 7/2000 | Chamberlain et al. | 435/369 |
| 6,346,421 B1 | 2/2002 | Anderson et al. | 436/177 |

OTHER PUBLICATIONS

Zolotor et al., *Equilibrium centrifugation of DNA, RNA and Pliovirus in Density Gradients of Cesium Oxalate and Cesium Acetate*, Biochimica et Biophysica Acta, 1967, 145(1) 52–59 (1967).

* cited by examiner

*Primary Examiner*—Jan Ludlow
(74) *Attorney, Agent, or Firm*—Howrey Simon Arnold & White, LLP

(57) ABSTRACT

Methods of forming a density gradient by applying a centrifugal field to a solution of one or more metal ion chelate complexes are disclosed. The density gradients are self-forming equilibrium gradients and are useful for separating biological particles by ultracentrifugation. Also disclosed are methods of separating biological particles according to their density. Also disclosed are density gradients of lipoprotein particles and one or more metal ion chelate complexes, wherein the lipoprotein particles are partitioned along the density gradient according to their particle density.

31 Claims, 5 Drawing Sheets

DENSITY GRADIENT SOLUTIONS OF METAL ION CHELATE COMPLEXES

CROSS-REFERENCE TO RELATED APPLICATIONS

This application claims the benefit of U.S. Provisional Application No. 60/274,045, filed Mar. 7, 2001, the entire contents of which are incorporated herein by reference.

BACKGROUND OF THE INVENTION

Centrifugation, the use of centrifugal force to separate particles, has been used for decades. Samples comprising the particles suspended in a medium are spun in a rotor at a high rate of speed and centrifugal force causes the particles to move outwardly from the rotational center of the rotor towards the periphery. This movement is known as sedimentation. The sedimentation rate is dependent upon several factors such as the rotational speed, the density and viscosity of the medium, the density of the particle, the size and the shape of the particle. The particles are separated in space by the differing distances they traverse along a centrifugal force vector. The degree of separation along this force vector determines the degree of resolution with which particles may be separated.

In density gradient ultracentrifugation, the density of the suspension medium varies in a known manner from one end of the centrifuge tube to the other. When the particle under the influence of centrifugal force reaches the point of its isopycnic density, i.e., when the density of the surrounding liquid is equal to the density of the particle, the particle it will cease to migrate along the force vector.

Solute systems used to establish density gradients for ultracentrifugation include inorganic salts (cesium chloride, potassium bromide, sodium chloride), sucrose and several commercially available solutes such as Ficoll®, a synthetic polysaccharide made by crosslinking sucrose; Percoll™, a suspension of silica particles coated with polyvinylpyrrolidone; and Nycodenz®, a derivative of the synthetic molecule metrizoic acid (metrizamide). Iodixinol, a dimer of Nycodenz®, is also used widely.

These solute systems are plagued by several deficiencies. The inorganic salts must be used at high concentrations which may cause dehydration of biological particle analytes, thus changing the physical/chemical properties of the analytes. The solutes can also alter the physical/chemical properties of the particles by forming solvation spheres around the particles.

Sucrose and its polysaccharide derivatives tend to form highly viscous solutions at high solute densities. This dramatically increases the time required to reach sedimentation equilibrium.

Because the density of a solution is proportional to the concentration of solute, density gradients are typically formed using the above solutes by layering solutions of lower concentration on top of solutions of higher concentration. For example, a density gradient can be made by layering solutions of sucrose one on top of another to form a gradient from 10–40% sucrose from the top of the tube to the bottom. This process is time consuming and may suffer from poor reproducibility from sample to sample.

Various methods and devices for forming density gradients have been explored in an effort to improve the ease and reproducibility of using the above solute systems. For example, U.S. Pat. No. 5,171,539 describes an apparatus for generating a continuous solution gradient wherein solutions of differing concentrations are layered in a tube and the tube is disposed at an angle with respect to the vertical. The tube is rotated for a period of time thereby generating a continuous solution gradient.

U.S. Pat. No. 4,290,300 describes a device having a chamber for a heavy concentration of sucrose and a chamber for a light concentration of sucrose. The relative rate of release from the two chambers is controlled by the pressure in the chambers, thus allowing the formation of linear or exponential density gradients.

An alternate method would be to use a solute system where a density gradient "self-forms" when the system is exposed to a centrifugal field. U.S. Pat. No. 4,480,038 describes a self-forming gradient using 60% Percoll™ containing 25 mM sucrose.

U.S. Pat. No. 5,985,037 describes a self-forming density gradient created by applying a centrifugal field to a solution that contains 27–33% Percoll™ and 36–44% sugar.

These self-forming gradients are easier to reproduce, but they require a high concentration of solute. The gradient environment therefore differs significantly from physiological conditions. High solutes concentrations also increase the viscosity of the solution thereby increasing the length of time that is required for the particles to reach sedimentation equilibrium. Further, the availability of a self-forming density gradient that avoids the use of silica-based solutes is desirable because silica-based solutes do not mimic physiological conditions.

SUMMARY OF THE INVENTION

One aspect of the present invention is a method of forming a density gradient, the method comprising: providing a solution of one or more metal ion chelate complexes and applying a centrifugal field to the solution until a density gradient is formed.

A further aspect of the invention is a method of separating particles according to their density, the method comprising: providing a composition comprising the particles and a solution of one or more metal ion chelate complexes; and applying a centrifugal field to the composition until the solution has formed a density gradient and the particles have partitioned along the density gradient.

A still further aspect of the present invention is a density gradient comprising one or more metal ion chelate complexes.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
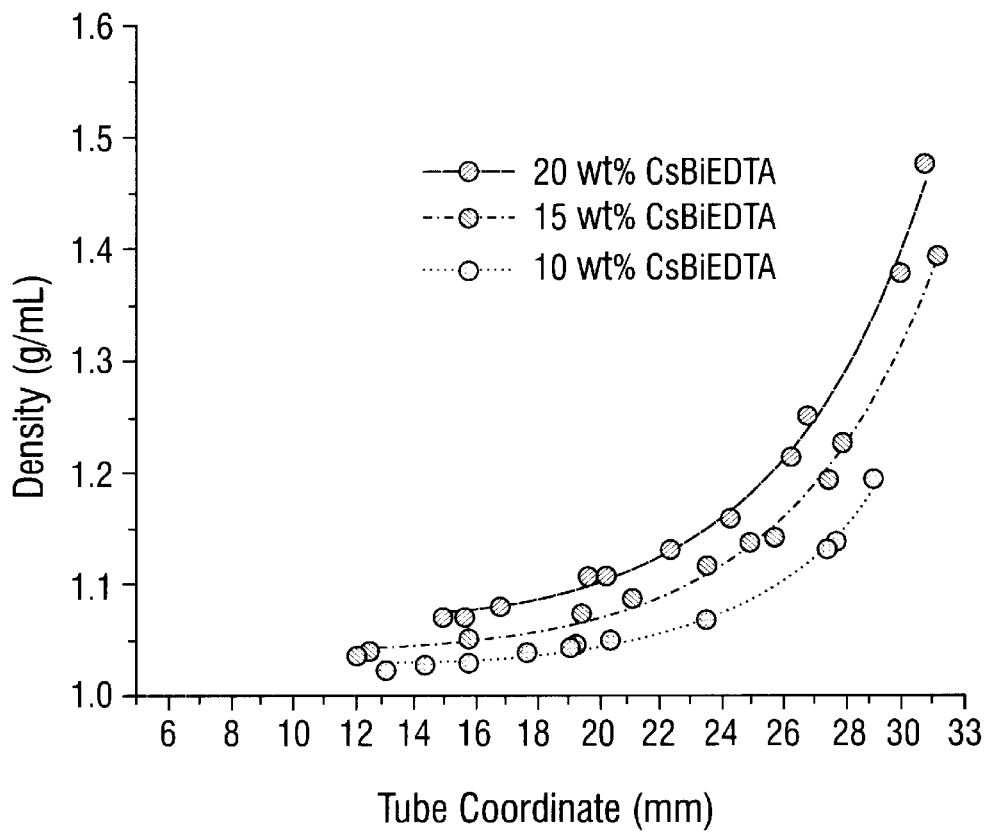
FIG. 1 shows a plot of the density gradients as a function of position within the tubes for solutions of 10, 15 and 20 wt. % CsBiEDTA. The tube coordinates were measured in mm with 0 mm representing the top of the tube.

One aspect of the present invention is a method of forming a density gradient, the method comprising providing a solution of one or more metal ion chelate complexes and applying a centrifugal field to the solution until a density gradient is formed. The properties of the density gradient are a function of the particular metal ion chelate complex, the concentration of the solution, temperature and the magnitude of the centrifugal field.

As used herein, the term "metal ion chelate complex" refers to a complex formed between a metal ion and a chelating agent. The metal ion can generally be any metal ion. Metal ions of the present invention include, but are not limited to ions of copper, iron, bismuth, zinc, cadmium, calcium, thorium and manganese. Presently preferred metal ions are ions of copper, iron, calcium, thorium and bismuth.

One of skill in the art would recognize the term "chelating agent" to refer to a particular type of ligand that can form a complex with a metal ion, wherein the ligand comprises more than one atom having unshared pairs of electrons that form bonds or associations with the same metal ion. Chelating agents are also referred to as polydentate ligands. Examples of chelating agents according to the present invention include, but are not limited to oxalate, ethylenediamine, diethlyenetriamine, 1,3,5-triaminocyclohexane and ethylenediaminetetraacetic acid (EDTA). EDTA is capable of donating up to six unshared pairs of electrons to the metal chelate complex and is a presently preferred chelating agent.

Metal ion chelate complexes of the present invention may sometimes require one or more positively charged counter-ion to balance the overall charge of the complex. Examples of counter-ions include, but are not limited to lithium, sodium, potassium, cesium, magnesium, calcium and ammonium as well as counter-ions such as ammonium complexes, for example tetrabutylammonium. When more than one counter-ion is required to balance the overall charge, the counter-ions can be mixed. For example, a metal ion chelate complex requiring two positive charges can have one positive charge supplied by sodium and the other by potassium.

The properties of the density gradient can be modified by choosing different combinations of metal ions, chelating agents and counter ions. Examples of suitable metal ion chelate complexes include, but are not limited to NaCuEDTA, NaFeEDTA, NaBiEDTA and CsBiEDTA. CsBiEDTA is a presently preferred metal ion chelate complex. Solutions of more than one metal ion chelate complex can also be used to form density gradients according to the present invention.

The concentration of the metal ion chelate complex can generally be any concentration range. The concentration of the metal ion chelate complex solution is typically about 0.01 M to about 0.7 M, and more typically about 0.1 M to about 0.3 M. In general, a lower concentration results in a lower density range while a more concentrated solution typically yields a higher range of densities.

Density gradients of the present invention may be disposed in any suitable container. Density gradients of the present invention are typically disposed within a tube, particularly within a centrifuge tube. The centrifugal field can be applied to the solution by spinning the tube in a rotor. The spin rate affects the speed at which the density gradient is formed, a faster spin rate typically resulting in faster gradient formation. Rapid gradient formation is desirable because it reduces the time required for the separation. However, too rapid of a gradient formation may adversely affect particle separation because the particles do not have a chance to find their isopycnic point before the gradient becomes too steep. Thus, the spin rate must be experimentally optimized for a given set of conditions and analytes. Typically spin rates are about 10,000 rpm to about 200,000 rpm.

Any of the various rotor/tube configurations know in the art can be used with the gradients of the present invention. Examples include fixed angle rotors, vertical tube rotors and swinging bucket rotors. A typical rotor configuration is a fixed angle of about 30°.

According to one embodiment of the present invention, the density gradients formed according to the instant methods are essentially exponential density gradients. That is, the density of the solution varies essentially exponentially as a function of position from one end of the tube to the other. Exponential geometry of a density gradient is an indication that the gradient is at equilibrium. This type of gradient is ideal for isopycnic mode separations wherein the particles migrate through the gradient until they reach a position that is equal to their own density. Isopycnic mode separations are desirable because they reflect the true equilibrium densities of the particles.

Solute systems that self-form equilibrium gradients are quite rare in the art. Optiprep® and Percoll™ have been shown to self-form gradients. However, at high rotor speeds such as those required to separate small biological particles, the gradients are too steep to achieve effective separation. This confines their applicability to larger particles such as cells and organelles.

In contrast, the methods of the present invention result in self-forming equilibrium gradients that are useable at high rotor speeds. These gradients are therefore useful for separating smaller biological particles such as lipoproteins.

An advantageous aspect of the present invention is that many of the metal ion chelate complexes have characteristic strong absorbances in the UV and visible spectrum. The magnitude of the absorbance is proportional to the concentration of the solution and can therefore be correlated to the density of the solution. This allows the determination of the density of the solution at any point along the gradient by determining the absorbance of the solution at that point.

For example, a calibration curve relating the density of a metal ion chelate complex solution to its absorbance at a given wavelength can be generated using standard solutions of known density. Next, a sample of solution from the gradient can be removed from a precisely known place in the tube and its density determined from its absorbance, with reference to the calibration curve. Depending on the gradient concentration, it may be helpful to dilute the gradient sample prior to measuring its absorbance. Such methods of generating and using a calibration curve are familiar to one of skill in the art.

Accordingly, one embodiment of the present invention further comprises determining the density of the solution at a specific point along the density gradient by determining the magnitude of the absorbance of the solution at the point and correlating the magnitude of the absorbance to the density.

An alternative method for determining the density at a given point along the density gradient is to include internal density markers in the solution of the metal ion chelate complex. These are compounds that are visible or otherwise detectable by some method such as fluorescence or luminescence. The density markers partition in the gradient according to their density, thus providing a detectable indication of the density at that given point in the gradient.

A further aspect of the present invention is a density gradient comprising a solution of one or more metal ion chelate complexes. Preferred concentration gradients are prepared according to the above describe methods. These concentration gradients afford several advantages over gradients known from the prior art. Concentration gradients of the present invention are typically less viscous than those of the prior art, and therefore particles reach separation equilibrium in less time with the present gradients. Also, the environment within the present gradients more closely resembles biological conditions than does the environment of other gradients. Gradients of the present invention also reduce solvation effects and dehydration of biological samples. The particle densities determined using gradients of the present invention are therefore closer to their in vivo densities.

A still further aspect of the invention is a method of separating particles by their density, the method comprising providing a composition comprising the particles and a solution of one or more metal ion chelate complexes and applying a centrifugal field to the composition until the solution has formed a density gradient and the particles have partitioned along the density gradient according to their density. This method of separating particles takes advantage of density gradients prepared according to the above described methods.

Generally, any type of particle that is amenable to density gradient ultracentrifugation can be separated using density gradients according to the present invention. Examples include lipoproteins, proteins, various microorganisms, various cell types and cell constituents and DNA.

Density gradients according to the instant invention are particularly suited for separating lipoproteins of differing densities from one another. Lipoproteins are typically divided into classes based on their density and compositions. Such classes include very low density lipoprotein (VLDL), low density lipoproteins (LDL), intermediate density lipoproteins (IDL), high density lipoproteins (HDL) and lipoprotein(a) (Lp(a)). The relative amounts of these lipoproteins in the blood are important clinical diagnostic indicators for coronary heart disease.

According to one embodiment of the present invention, the particles to be separated are dispersed in a solution of the metal ion chelate complex prior to the application of the centrifugal field. A centrifugal field is then applied until a density gradient forms in the solution and the particles are distributed in the gradient according to their densities. Isopycnic separations are typically achieved most quickly by this method.

Isopycnic mode separations are particularly suitable for the analysis of lipoproteins because the isopycnic mode yields substantial information about the equilibrium density of the lipoproteins. This information is relevant as a clinical diagnostic for coronary heart disease.

Density gradients of the present invention can be used for other modes of separation. For example, in the rate-zonal mode, the particles can be disposed as a layer on top of the solution of the metal ion chelate complex. During centrifugation the particles are separated according to their sedimentation coefficient, which is dependent on their size. This technique is frequently used to calculate the molecular weight of particles. After a sufficient amount of time these separations become isopycnic.

In the floatation mode, the sample is adjusted to a higher density and then solutions of lower densities are layered above the sample to form a discontinuous gradient. During centrifugation the particles are separated according to their densities but they are confined to the zones created by the different density layers. Unless the spinning is continued for a long time and the discontinuous gradient has a chance to become continuous, it is not possible to determine the equilibrium densities of the particles using this mode. However, it is possible to determine density ranges for a group of the particles.

The instant method can further comprise treating the analyte particles so that they can be more easily detected on the gradient. An example of such a treatment is exposing the analyte particles to a stain or dye that has some attraction to the analyte particles and that renders the particles visible or detectable by some means such as spectroscopic or radiographic techniques. Staining and dying techniques for biological particles are well known in the art. An example of a common dye for biological samples is Sudan Black.

According to a presently preferred embodiment of the present invention, the analyte particles are exposed to a stain or dye having a marker that is detectable by a spectroscopic or radiographic technique and wherein, when the particles are separated in the gradient according to their densities, the amount of marker that is detected at a given position in the gradient is proportional to the number of analyte particles that are present at the position. This allows quantitative characterization of particle density distributions of samples.

According to one embodiment of the present invention, a mixture of particles is exposed to a stain which comprises a fluorescent marker. A particularly suitable type of fluorescent dye for lipoproteins is fluorescent phospholipids. One examples is NBD C6-ceramide (Molecular Probes, Eugene, Oreg., Cat. No. N-1154). The stained particles are then suspended in a solution of a metal ion chelate complex. The solution is exposed to a centrifugal field until a density gradient forms in the solution and the particles are partitioned in the gradient according to their density. The distribution of the particles is then analyzed by exciting the fluorescence marker and detecting the resulting fluorescence bands along the gradient. Methods of fluorescence excitation and detection are well known to those of skill in the art. A particularly preferred method is to excite the fluorescent marker with the characteristic excitation wavelength and to photograph the fluorescence emission with a camera. The camera is preferably placed at an angle relative to the excitation vector and the lens is preferably filtered to allow only a narrow band of radiation at the fluorescence wavelength to enter the camera. According to this embodiment, the signal-to-noise ratio is maximized when the Stokes shift of the fluorescent marker is great enough that there is a substantial difference between the excitation and emission radiation wavelengths. The signal-to-noise ratio can also be maximized by adjusting the shutter speed of the camera.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

An essentially linear calibration curve was generated relating the density of known standard solutions of CsBiEDTA to the absorbance of the solutions at 264 nm. Solutions of 10, 15 and 20 wt % of CsBiEDTA were prepared and 1.5 mL ultracentrifuge tubes containing the solutions were spun for 4 hours at 120,000 rpm at 20° C. in a Beckman ultracentrifuge rotor using a 30° fixed angle. The resulting density gradients were analyzed by withdrawing 10 $\mu$L aliquots of solution from precisely known points in the tubes. The aliquots were diluted by a factor of $1 \times 10^4$ and the absorbance of the resulting solutions were determined at 264 nm. The calibration curve was used to back-calculate the density at the points along the gradient. FIG. 1 shows a plot of the density gradients as a function of position within the tubes. The tube coordinates were measured in mm with 0 mm representing the top of the tube.

EXAMPLE 2

Blood serum samples were prepared by allowing fresh-drawn blood to clot for 15 minutes and then centrifuging at 3000 rpm to obtain the serum. 100 $\mu$L of serum was stained with 8 $\mu$L of Sudan Black and diluted with 292 $\mu$L of water. 200 $\mu$L of the resulting solution was layered over 900 $\mu$L of 0.25 M CsBiEDTA (density=1.103 g/ml) and a similarly prepared sample was layered over 900 $\mu$L of 0.74 M CsCl (density=1.00 g/ml). Both tubes were spun for 2 hours at 120,000 rpm followed by 2 hours at 100,000 rpm.

Figure 2:
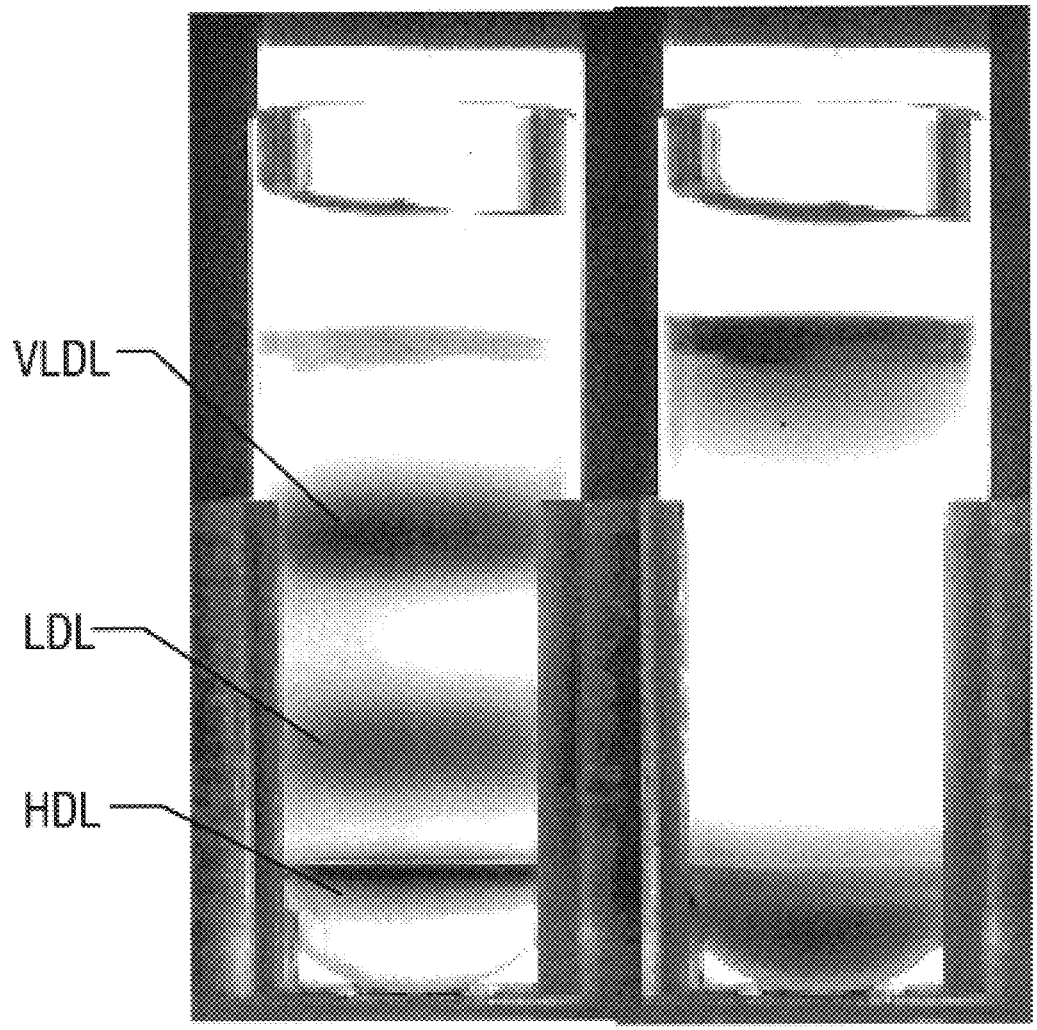
FIG. 2 shows gradients of blood serum samples layered over 900 $\mu$L of 0.25 M CsBiEDTA and over 900 $\mu$L of 0.74 M CsCl. Both tubes were spun for 2 hours at 120,000 rpm followed by 2 hours at 100,000 rpm.

FIG. 2 shows the resulting gradients for the two samples. The CsBiEDTA formed an effective gradient and resolved the bands corresponding to VLDL, LDL and HDL. CsCl did not appear to form an effective gradient. The VLDL and LDL remained at the top of the tube and the HDL migrated to the bottom of the tube.

EXAMPLE 3

Density gradients of CsBiEDTA and Iodixinol (Optiprep) were compared. Serum samples, prepared as described above, were layered onto 0.25 M CsBiEDTA and onto 19.5 wt. % Iodixinol, each contained in separate centrifuge tubes. A second pair of runs were conducted wherein the serum samples were dispersed in each density matrices. The four tubes were spun for four hours at 120,000 rpm. The rotor was stopped every hour and the tubes were photographed.

Figure 3:
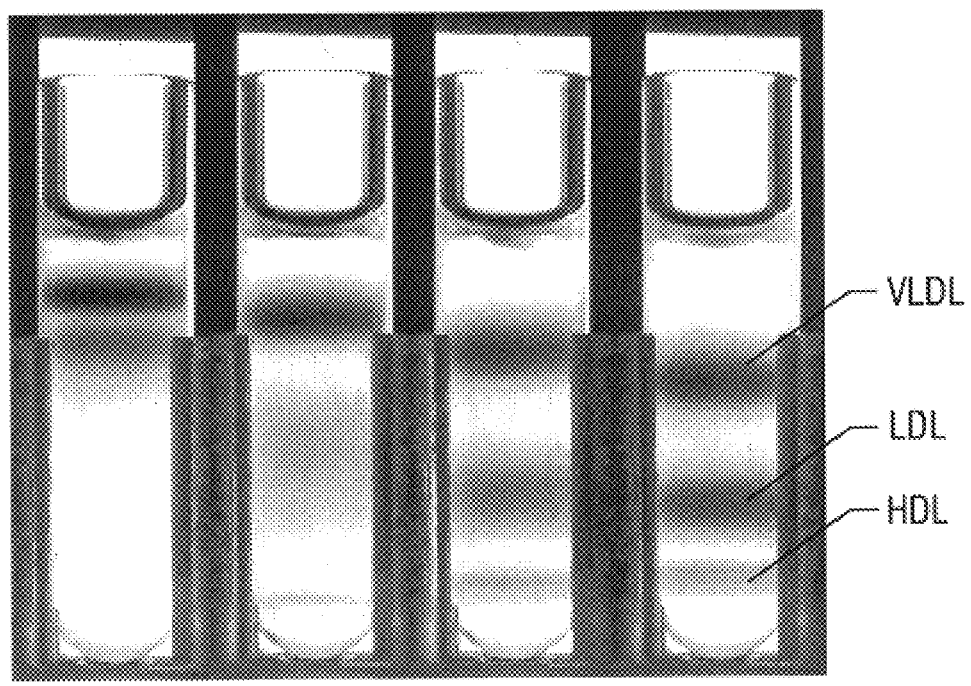
FIG. 3 shows gradients of a blood serum sample layered over 900 $\mu$L of 0.25 M CsBiEDTA. The tube was spun at 120,000 rpm and photographed after each hour for 4 hours.
Figure 4:
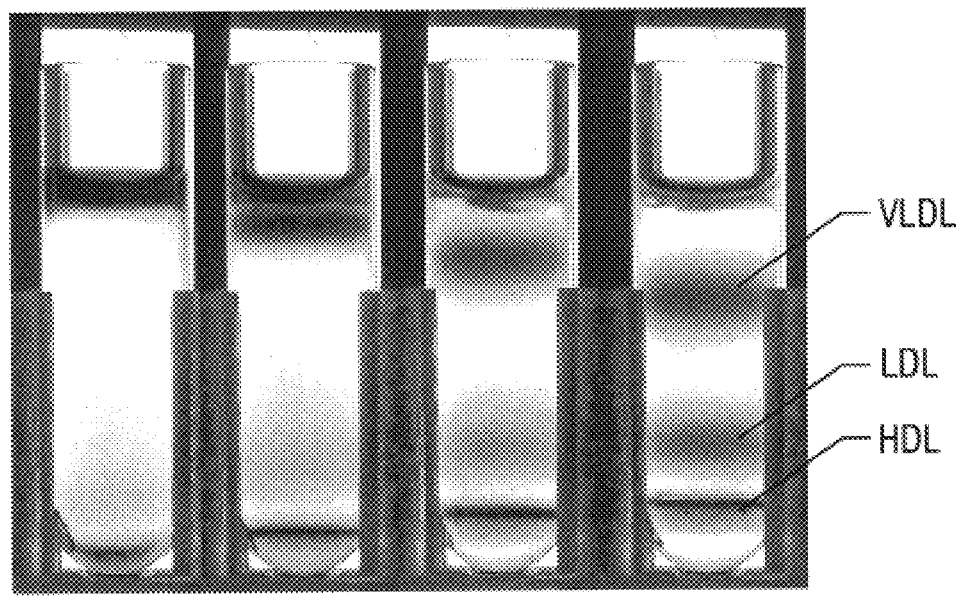
FIG. 4 shows gradients of a blood serum sample dispersed in 900 $\mu$L of 0.25 M CsBiEDTA. The tube was spun at 120,000 rpm and photographed after each hour for 4 hours.

FIGS. 3 and 4 show the CsBiEDTA gradients after each hour. Excellent separation was achieved after 4 hours with both the layered and the dispersed CsBiEDTA samples. The dispersed sample (FIG. 4) yielded slightly better separation than the layered sample (FIG. 3).

Figure 5:
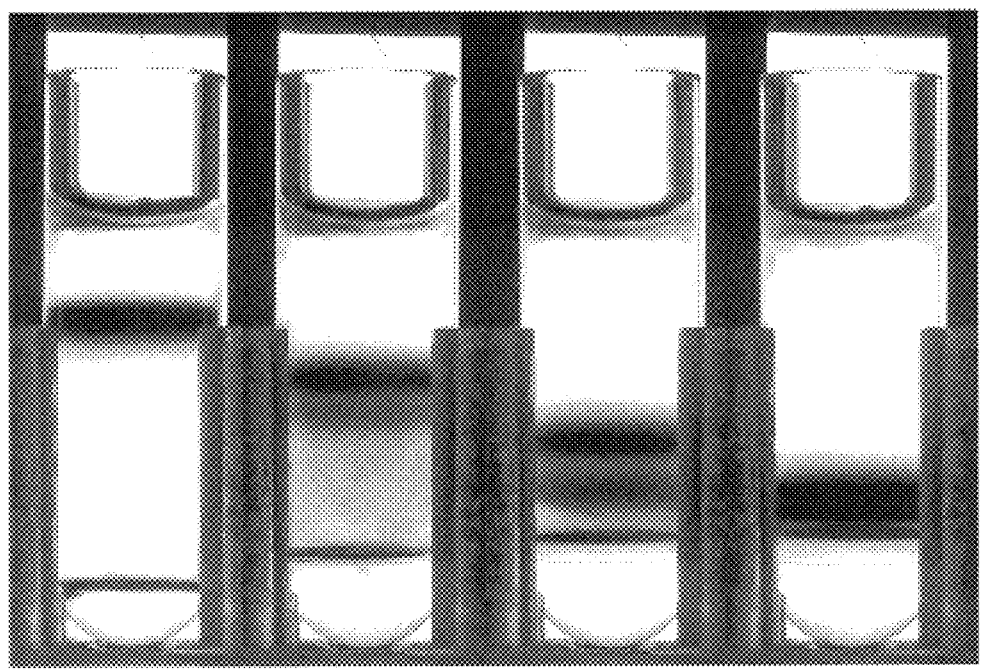
FIG. 5 shows gradients of a blood serum sample layered over 900 µL of 19.5 wt. % Iodixinol. The tube was spun at 120,000 rpm and photographed after each hour for 4 hours.
Figure 6:
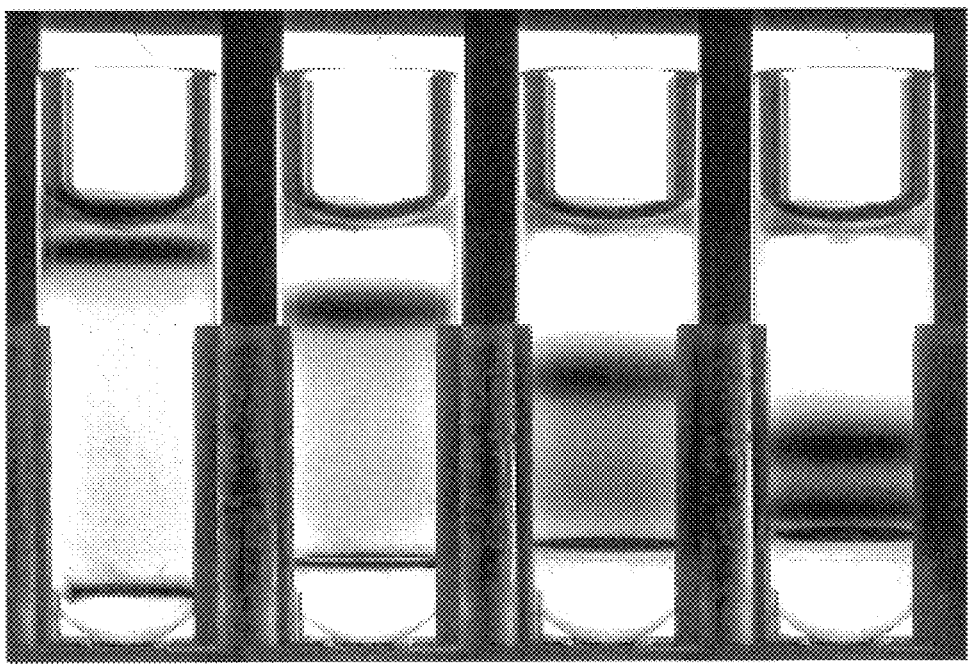
FIG. 6 shows gradients of a blood serum sample dispersed in 900 µL of 19.5 wt. % Iodixinol. The tube was spun at 120,000 rpm and photographed after each hour for 4 hours.

The Iodixinol samples yielded poor results for both the layered (FIG. 5) and the dispersed (FIG. 6) trials. A steep gradient formed very rapidly in Iodixinol so that the lipoproteins did not have time to reach their isopycnic point before the gradient became so steep that it was not capable of resolving the lipoproteins.

EXAMPLE 4

A lyophilized serum sample was reconstituted with 500 $\mu$L of water. A volume of 78 $\mu$L of each of the samples were stained with 5 $\mu$L of NBD C6-ceramide for 30 minutes. Water was added to each to bring the volume up to 650 $\mu$L. The samples were mixed by inversion and then spun for 4 minutes at 7000 rpm. A volume of 550 $\mu$L of each of the samples was then mixed with 550 $\mu$L of 20 wt % CsBiEDTA in ultracentrifuge tubes. The tubes were spun for 4 hours 40 minutes at 120,000 rpm and 20° C.

The gradient was exposed to excitation light from a halogen light bulb filtered through a blue-violet band pass filter (Edmund Industrial Optics). The tube was photographed using a camera equipped with Syber Green filter (Kodak). Photographs were taken using shutter speeds of $\frac{1}{30}$, $\frac{1}{15}$, $\frac{1}{8}$ and $\frac{1}{4}$ seconds.

Figure 7:
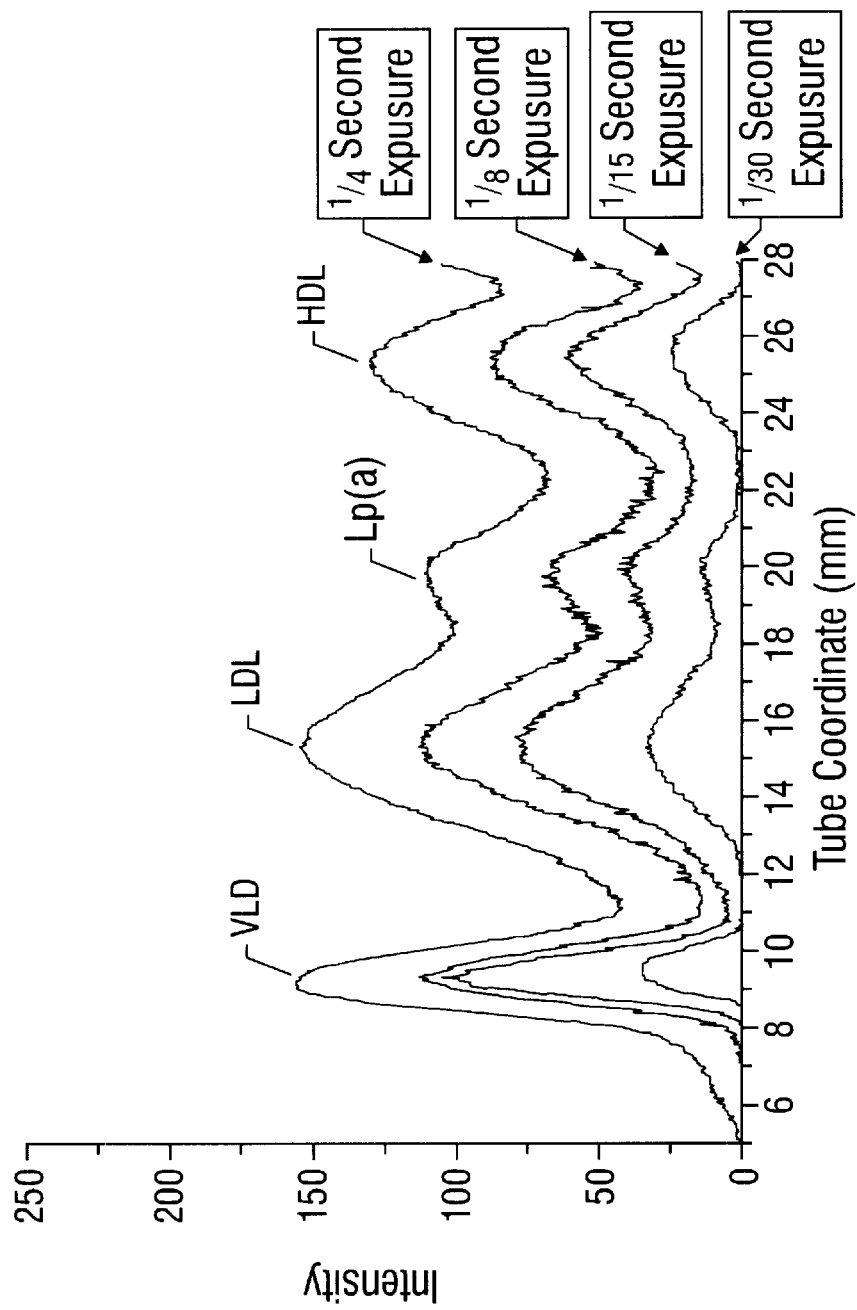
FIG. 7 shows the intensity of fluorescence as a function of tube coordinate at shutter speeds of 1/30, 1/15, 1/8 and 1/4 seconds for a fluorescence-stained mixture of blood serum. The tube was spun for 4 hours and 40 minutes at 120,000 rpm and 20° C. using a density gradient of 10 wt % CsBiEDTA. The tube coordinate was measured in mm with 0 mm representing the top of the tube.

The intensity of fluorescence as a function of tube coordinate at each of the shutter speed is shown in FIG. 7. The optimum shutter speeds are $\frac{1}{15}$ and $\frac{1}{8}$. The $\frac{1}{30}$ shutter speed photos are somewhat faint while the $\frac{1}{4}$ shutter speed photos have greater than optimal background exposure.

The profiles of the lipoproteins observed using the fluorescent dye are slightly different from those typical observed using Sudan Black because the LDL band is more buoyant with the fluorescent dye. This suggests that Sudan Black increases the density of the LDL. The fluorescent dye method provides a density that is more similar to the in vivo value. Also, a band associated with Lp(a) was detectable using this method.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of forming a density gradient, the method comprising:
    applying a centrifugal field to a solution of one or more metal ion chelate complexes until the one or more metal ion chelate complexes forms a density gradient.

2. The method of claim 1 wherein the average concentration of the metal ion chelate complex is about 0.01 M to about 0.7 M.

3. The method of claim 1 wherein the average concentration of the metal ion chelate complex is about 0.1 M to about 0.3 M.

4. The method of claim 1 wherein the metal ion chelate complex is selected from the group consisting of NaBiEDTA, CsBiEDTA, NaFeEDTA, NaCuEDTA, and mixtures thereof.

5. The method of claim 1 wherein the metal ion chelate complex is CsBiEDTA.

6. The method of claim 1 herein the solution is disposed within a tube and the centrifugal field is applied by spinning the tube in a rotor at a rate of about 10,000 rpm to about 200,000 rpm.

7. The method of claim 1 wherein the solution is disposed within a tube and the centrifugal field is applied by spinning the tube in a rotor for about 0.5 hours to about 8 hours.

8. The method of claim 1 herein the solution is disposed within a tube and the centrifugal field is applied by spinning the be in a rotor for about 0.5 hours to about 2 hours.

9. The method of claim 1 wherein the density gradient is essentially exponential.

10. The method of claim 1 further comprising determining the density of the solution at a specific point along the density gradient.

11. The method of claim 10 wherein the density of the solution at a specific point along the density gradient is determined by determining the magnitude of the absorbance of the solution at the point and correlating the magnitude of the absorbance to the density.

12. A method of separating particles according to their density, the method comprising:
providing a composition comprising the particles and a solution of one or more metal ion chelate complexes; and
applying a centrifugal field to he composition until the one or more metal ion chelate complexes form a density gradient and the particles have partitioned along the density gradient according to their density.

13. The method of claim 12 wherein the average concentration of the metal ion chelate complex solution is about 0.01 to about 0.7 M.

14. The method of claim 12 wherein the average concentration of the metal ion chelate complex solution is about 0.1 M to about 0.3 M.

15. The method of claim 12 wherein the metal ion chelate complex is selected from the group consisting of NaBiEDTA, CsBiEDTA, NaFeEDTA, NaCuEDTA, and mixtures thereof.

16. The method of claim 12 wherein the metal ion chelate complex is CsBiEDTA.

17. The method of claim 12 wherein the composition is disposed within a tube and the centrifugal field is applied by spinning the tube in a rotor at a rate of about 10,000 rpm to about 200,000 rpm.

18. The method of claim 12 wherein the composition is disposed within a tube and the centrifugal field is applied by spinning the tube in a rotor for about 0.5 hours to about 8 hours.

19. The method of claim 12 wherein the composition is disposed within a tube and the centrifugal field is applied by spinning the tube in a rotor for about 0.5 hours to about 2 hours.

20. The method of claim 12 herein the density gradient is essentially exponential.

21. The method of claim 12 wherein prior to applying the centrifugal field, the particles are disposed as a layer on the solution.

22. The method of claim 12 wherein prior to applying the centrifugal field, the particles are dispersed throughout the solution.

23. A density gradient formed from one or more metal ion chelate complexes.

24. The density gradient of claim 23 wherein the average concentration of the metal ion chelate complex is about 0.01 to about 0.7 M.

25. The density gradient of claim 23 wherein the average concentration of the metal ion chelate complex is about 0.1 M to about 0.3 M.

26. The density gradient of claim 23 wherein the metal ion chelate complex is selected from the group consisting of NaBiEDTA, CsBiEDTA, NaFeEDTA, NaCuEDTA, and mixtures thereof.

27. The density gradient of claim 23 wherein the metal ion chelate complex is CsBiEDTA.

28. The density gradient of claim 23 wherein the density gradient is essentially exponential.

29. A composition comprising a density gradient of one or more metal ion chelate complexes and lipoprotein particles, wherein the lipoprotein particles are partitioned along the density gradient according to the density of the lipoprotein particles.

30. The composition of claim 29 wherein the metal ion chelate complex is selected from the group consisting of NaBiEDTA, CsBiEDTA, NaFeEDTA, NaCuEDTA, and mixtures thereof.

31. The composition of claim 29 wherein the metal ion chelate complex is CsBiEDTA.

* * * * *

UNITED STATES PATENT AND TRADEMARK OFFICE
CERTIFICATE OF CORRECTION

PATENT NO.      : 6,593,145 B2
DATED           : July 15, 2003
INVENTOR(S)     : Ronald D. Macfarlane and Brian D. Hosken It is certified that error appears in the above-identified patent and that said Letters Patent is hereby corrected as shown below:

Column 8,
Lines 64-67, claim 6 should read as follows:
6. The method of claim 1 wherein the solution is disposed within a tube and the centrifugal field is applied by spinning the tube in a rotor at a rate of about 10,000 rpm to about 200,000 rpm.

Column 9,
Lines 4-6, claim 8 should read as follows:
8. The method of claim 1 wherein the solution is disposed within a tube and the centrifugal field is applied by spinning the tube in a rotor for about 0.5 hours to about 2 hours.
Lines 16-24, claim 12 should read as follows:
12. A method of separating particles according to their density, the method comprising:
    providing a composition comprising the particles and a solution of one or more metal ion chelate complexes; and
    applying a centrifugal field to the composition until the one or more metal ion chelate complexes form a density gradient and the particles have partitioned along the density gradient according to their density.

Column 10,
Lines 5-6, claim 20 should read as follows:
20. The method of claim 12 wherein the density gradient is essentially exponential.

Signed and Sealed this

Thirteenth Day of January, 2004

JON W. DUDAS
*Acting Director of the United States Patent and Trademark Office*